(12) United States Patent
Tuller et al.

(10) Patent No.: US 6,370,955 B1
(45) Date of Patent: Apr. 16, 2002

(54) HIGH-TEMPERATURE BALANCE (75) Inventors: Harry L. Tuller, Wellesley, MA (US); Holger Fritze, Wernigerode (DE)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/449,576

(22) Filed: Nov. 29, 1999

Related U.S. Application Data (63) Continuation-in-part of application No. 09/449,334, filed on Nov. 24, 1999, now abandoned
(60) Provisional application No. 60/139,168, filed on Jun. 15, 1999.

(51) Int. Cl.[7] ............................................. G01H 13/00
(52) U.S. Cl. ...................... 73/579; 204/298.03; 427/10; 427/9; 427/99
(58) Field of Search .......................... 73/579, 574, 602; 310/360, 366, 311; 204/298.01, 298.02, 298.03; 427/8, 9, 10, 96, 99, 100

(56) References Cited

U.S. PATENT DOCUMENTS

| | | | |
|---|---|---|---|
| 4,207,836 A | 6/1980 | Nonaka | 118/664 |
| 4,311,725 A | 1/1982 | Holland | 427/10 |
| 4,588,942 A | 5/1986 | Kitahara | 324/71.5 |
| 4,817,430 A | 4/1989 | Benes et al. | 73/579 |
| 5,025,664 A * | 6/1991 | Kendrick et al. | 73/579 |
| 5,112,642 A | 5/1992 | Wajid | 427/10 |
| 5,117,192 A | 5/1992 | Hurd | 324/727 |
| 5,321,719 A | 6/1994 | Reed et al. | 374/14 |
| 5,605,490 A | 2/1997 | Laffey et al. | 451/36 |
| 5,686,779 A | 11/1997 | Vig | 310/366 |
| 5,744,902 A | 4/1998 | Vig | 310/360 |

FOREIGN PATENT DOCUMENTS

| | | |
|---|---|---|
| DE | 44 04 309 A1 | 8/1995 |
| GB | 2 088 058 A | 6/1982 |
| JP | 57153208 | 9/1982 |
| JP | 57153208 A1 * | 9/1982 |
| JP | 03271364 | 12/1991 |
| WO | WO 96/31773 | 10/1996 |
| WO | WO 96/35103 | 11/1996 |
| WO | WO 99/28735 | 6/1999 |

OTHER PUBLICATIONS

Damjanovic, Dragan, "Materials for High Temperature Piezoelectric Transducers," in Current Opinion in Solid State & Materials Science 1998, 3:469–473.

Krempl, P. et al, "Gallium phosphate, $GaPO_4$: a new piezoelectric crystal material for high–temperature sensorics," Sequoia, S.A., Lausanne, vol. 61; No. 1–3, May 1, 1997, pp. 361–363.

(List continued on next page.)

*Primary Examiner*—Hezron Williams
*Assistant Examiner*—Rose M. Miller
(74) *Attorney, Agent, or Firm*—Hamilton, Brook, Smith & Reynolds, P.C.

(57) ABSTRACT

A high-temperature balance includes a piezoelectric material, such as langasite, that is stable at high temperatures. The frequency response of the balance is monitored to determine the change in mass of material deposited on the balance in a high-temperature environment. Accordingly, the balance can be used to monitor high-temperature deposition rates or to perform thermogravimetric analysis. The high-temperature balance of this invention can further be operated as a nanobalance to measure monolayer changes in film thickness.

40 Claims, 3 Drawing Sheets

OTHER PUBLICATIONS

Gotalskaya, A.N. et al., "Peculiarities of Technology, Physical Properties and Applications of New Piezoelectric Material Langasite ($LA_3CA_5SIO_{14}$)," IEEE International Frequency Control Symposium, vol. SYMP. 47, Jun. 2, 1993, pp. 339–347.

Spassov, L., et al., "Piezoelectric sorption sensor for mercury vapors in air using a quartz resonator," Review of Scientific Instruments, American Institute of Physics, vol. 64, No. 1, Jan. 1993, pp. 225–227.

Détaint, J., et al., "Optimisation of the Design of the Resonators using the New Materials: Application to Gallium Phosphate and Langasite," IEEE International Frequency Control Symposium, New York, May 28, 1997, pp. 566–578.

Bezdelkin V.V. et al., "Fundamental characteristics of thickness vibrations of langasite plates for baw resonators," Journal De Physique IV, Editions De Physique, Les Ulis, Cedex, France, vol. 4, Aug. 1994, pp. 139–156.

* cited by examiner

HIGH-TEMPERATURE BALANCE

RELATED APPLICATION

This application is a continuation-in-part of 09/449,334, filed on Nov. 24, 1999, now abandoned and having the same title and inventors as the present application; this application also claims the benefit of U.S. Provisional Application No. 60/139,168 filed Jun. 15, 1999, the entire teachings of which are incorporated herein by reference.

GOVERNMENT SUPPORT

The invention was supported, in whole or in part, by a grant, number DMR-9701699, from the National Science Foundation. The Government has certain rights in the invention.

BACKGROUND OF THE INVENTION

Numerous high-temperature processes exist in which mass is added to or removed from a substrate. Particular applications include vapor deposition processes such as chemical vapor deposition (CVD) and physical vapor deposition (PVD), which are routinely used in semiconductor wafer processing. Another application is thermogravimetric analysis (TGA) wherein a known mass of a composition is placed in a TGA chamber and heated in accordance with a graduated temperature profile and the change in mass is recorded as a function of change in temperature and/or time.

While atomic-level monitoring of changes in mass can be very valuable in both of these processes, known methods for monitoring the rate of deposition or evaporation of the composition generally lack the capability of providing precise measurements at elevated temperatures. Typically, measurements of changes in mass during a high-temperature process, such as TGA, are performed by a microbalance. Known microbalances typically measure a change in mass by measuring mechanical displacement. In one mass-balancing approach, a pivot is used to balance the weight of the support structure including deposited material with that of reference weights. Alternatively, the weight of the structure can be balanced with a variable electromagnetic force. In yet another embodiment, the compression of a spring upon which the support structure is mounted can be monitored to measure a change in weight.

The precision of these methods is limited because the weight of the structure will generally dwarf that of the material under analysis, thereby making changes in the mass of the material under analysis difficult to detect. Moreover, the existence of convection currents resulting from thermal gradients in the chamber can produce a buoyancy effect that reduces the perceived weight of the support structure.

SUMMARY OF THE INVENTION

In a method of this invention, a piezoelectric balance is heated, and the mass of a material deposited thereon is increased or decreased. The change in the mass of a material deposited on the piezoelectric balance is monitored by measuring the frequency response of the piezoelectric balance. Suitable applications include measurements of deposition, evaporation and/or post-growth oxidation or reduction.

An apparatus of this invention includes a deposition chamber or TGA chamber, a piezoelectric balance, and a heater for heating the piezoelectric balance. The piezoelectric balance includes a piezoelectric material that is stable at high temperatures. For example, the piezoelectric material can be a material having a $Ca_3Ga_2Ge_4O_{14}$-type structure, a member of the (Al, Ga)N system, or gallium phosphate. In preferred embodiments, the piezoelectric material is a composition that can undergo a vibrational resonance when a voltage is applied at temperatures above about 500° C. and, more preferably, at temperatures above about 600° C. A particularly preferred piezoelectric composition for use in this invention is langasite.

In accordance with one aspect of the invention, a workpiece is positioned in the deposition chamber along with the piezoelectric balance and the two are heated to approximately the same temperature while a film is simultaneously deposited upon each. Deposition can be carried out via chemical vapor deposition (CVD) or physical vapor deposition (PVD). The frequency response of the balance is measured to monitor the rate of deposition on the workpiece. In other embodiments, the frequency response of the piezoelectric balance can be monitored with changing temperature to determine the change in mass of a composition on the balance as a function of temperature. Alternatively, the frequency response of the piezoelectric balance can be monitored at an elevated temperature in a changing atmosphere to determine the change in mass of a composition on the balance as a function of changing gas composition. The frequency response of the balance can be monitored with an impedance analyzer electrically coupled to the balance.

This invention offers several advantages both over the use of conventional piezoelectric balances at or near room temperature and over the use of known methods for measuring change in mass at high temperatures.

First, the use of a high-temperature piezoelectric balance of this invention allows for in situ measurement of changes in mass at high temperatures. In this regard, the materials of this invention provide for operation over a much greater temperature range than that of more-conventional piezoelectrics, such as quartz. Consequently, these materials can be used to accurately measure changes in mass as a function of temperature across these extended ranges or as a function of gas composition at a given elevated temperature. Accordingly, piezoelectric balances of this invention can be used to reliably and accurately measure the rate of deposition in CVD or PVD processes, for example, where the substrate is heated to temperatures over 500° C. Similarly, the piezoelectric balances can serve as highly accurate and reliable detectors for monitoring change in mass resulting from oxidation and reduction during high-temperature post-growth annealing.

Second, relative to conventional methods, such as those involving weight measurements, the methods of this invention are capable of measuring changes in mass with remarkably-high precision. With measurements performed in accordance with this invention, frequency changes as fine as one hertz, which translates to a balance resolution of one part per million or finer where the operative frequency is 1–10 MHZ. Further, changes in the thickness of a deposited film can be detected on a monolayer basis, which is particularly useful in applications such as semiconductor processing where deposited layers may be a mere 5 to 10 atoms thick. Accordingly, the piezoelectric balance of this invention can be said to operate as a nanobalance. This level of precision is far superior to that of conventional methods for performing TGA.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
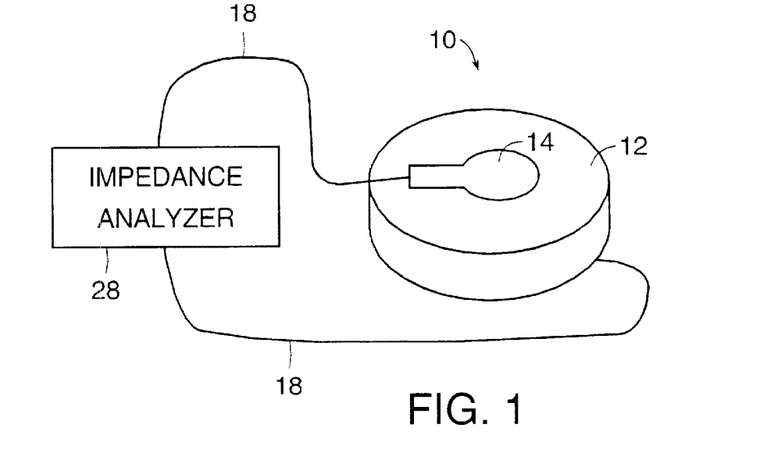
FIG. 1 is an illustration, partially schematic, of a high-temperature piezoelectric balance electrically coupled with an impedance analyzer for monitoring the vibrational resonance characteristics of the balance.

As illustrated in FIG. 1, a piezoelectric balance 10 for use with this invention includes a polished plate 12 formed of a piezoelectric material and a pair of electrodes 14 contacted to opposite surfaces of the plate 12. A pair of leads 18 join the electrodes 14 with an impedance analyzer 28. The impedance analyzer 28 applies an alternating voltage across the electrodes 14 causing atoms within the crystalline structure of the piezoelectric material to vibrate. The impedance analyzer 28 not only applies a voltage across the electrodes 14 but also measures the electrical admittance of the piezoelectric material as a function of frequency. Alternatively, a separate voltage source may be used.

The amplitude of the admittance signal provides an indication of the amplitude of vibration within the piezoelectric material. At any given temperature, the amplitude of vibration varies as a function of the frequency of the voltage source. The frequency at which the admittance is greatest is the "resonance frequency." At the resonance frequency, the atoms of the piezoelectric material oscillate with maximum amplitude. Conversely, the frequency of minimum admittance (and, consequently, minimum vibration amplitude) is known as the "antiresonance frequency."

The resonance frequency of the piezoelectric balance is a function of the dimensions of the balance. In preferred embodiments, the dimensions of the piezoelectric balance are selected to produce a resonance frequency of about 10 MHZ. Preferably, the electrodes 14 are key-hole shaped and formed of platinum.

Materials suitable for use with this invention include bulk single-crystal forms of piezoelectric materials that remain stable and sufficiently resistive at elevated temperatures so as to be able go into resonance, particularly at temperatures above 500° C. Suitably stable piezoelectric materials preferably are those that have only a single solid phase so as to prevent destructive changes in the crystalline structure with change in temperature. As an alternative to the use of a single crystal, multiple single-crystal films of a suitable piezoelectric material can be grown and stacked to form a layered structure. Further, the selected piezoelectric material should be non-reactive in the environments in which it operates and should not lose or gain oxygen at high temperatures.

Suitable piezoelectric materials include (1) materials of the $Ca_3Ga_2Ge_4O_{14}$-structure-type; (2) gallium phosphate ($GaPO_4$); and (3) materials in the (Al,Ga)N system. Specific members of the $Ca_3Ga_2Ge_4O_{14}$-structure-type that are suitable for use with this invention include langasite ($La_3Ga_5SiO_{14}$) and $La_3Ga_{5.5}M_{0.5}O_{14}$, where M is Ta or Nb. Langasite is particularly preferred because it will not undergo any phase transformations up to its melting point at 1470° C. Further, as is, langasite may be excited to exhibit bulk oscillations up to 750° C. and higher. Use of pure langasite will generally be limited by conductive losses. I.e., at particularly high temperatures, the conductivity of pure langasite will rise to a level at which the langasite can no longer be effectively vibrated when a voltage is applied. These conductive losses in the langasite can be compensated for by adding dopants that will increase the resistivity of the langasite and thereby enable its use at still higher temperatures.

Other piezoelectric materials conventionally used for piezoelectric transducers and sensors are generally ill-suited for use with this invention because they would fail to perform as desired at high temperatures. For example, lithium niobate ($LiNbO_3$) decomposes at 300° C. and is therefore unsuited for use at temperatures in that vicinity or above. Further, lithium borate ($Li_2B_4O_7$) exhibits phase transformation at approximately 500° C. and must therefore be maintained at a temperature below that level. Finally, quartz ($SiO_2$) undergoes high losses and a phase transformation that prevent its use above about 500° C.

Figure 2:
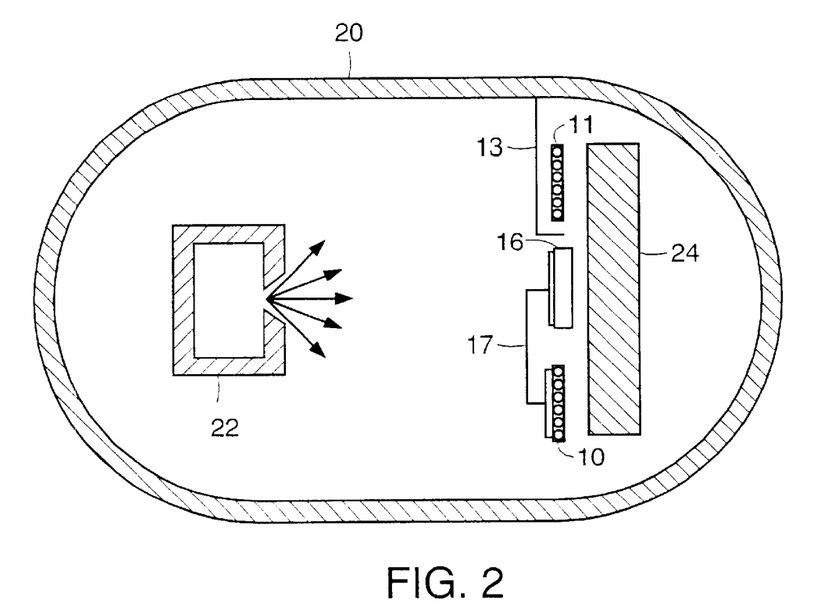
FIG. 2 is a deposition chamber including a high-temperature piezoelectric balance.

As shown in the embodiment illustrated in FIG. 2, the piezoelectric balance 10 can be positioned side-by-side with a workpiece 16. Alternatively, the balance can be mounted on the workpiece. In either case, the balance 10 is subject to the same conditions and processing as the workpiece 16. In the embodiment of FIG. 2, the workpiece 16 is a semiconductor wafer, and the balance 10 is positioned on or adjacent to the semiconductor wafer in a deposition chamber, where at least one thin film is deposited on or removed (i.e., evaporated) from the wafer in a fabrication procedure for forming a microelectronics device. Simultaneously, a thin film is also deposited on the balance 10, with the balance 10 maintained at the same, or nearly the same, temperature as the wafer. In preferred embodiments, the balance 10 and workpiece 16 are heated to a temperature of at least about 500° C., more preferably to a temperature of at least about 600° C. During the procedure, the frequency response of the balance 10 is measured to monitor the change in mass of the film or coating.

The apparatus of this embodiment further includes a vessel 20 which defines the deposition chamber as well as a source of vapor 22 (e.g., a gas supply line) connecting with the chamber to introduce reactant vapor for forming a film on the workpiece 16 and the balance 10. A heater 24 is also provided within the chamber for heating the workpiece 16 and the balance 10, preferably to the same temperature. The workpiece 16 is supported by a chuck and an impedance analyzer 28 (shown in FIG. 1) is electrically coupled to the balance 10. The impedance analyzer is used in a "passive" method for measuring frequency shift. Alternatively, an "active" method can be used to measure frequency shift. The active method, which is usually performed in commercial devices, uses the resonator as the frequency-determining device in an electronic feedback circuit. The passive method, as used with the apparatus of FIG. 1, yields more detailed information, such as the real and imaginary parts of the impedance. Additional discussion of the active method and a comparison of the active and passive methods is provided in *Precision Frequency Control*, Vol. 2, Chapter 8: "Bulk-Acoustic-Wave Oscillators" 47 (1985) and in A.

Bund. et al., "Validation of the Frequency Shift of Thickness-Shear-Mode Resonators in Liquids—Determination of the Activation Energy of Viscosity," 101 Ber. Bunsenges. Phys. Chem. (No. 12) 1960–62 (1997), the teachings of both references incorporated herein by reference in their entireties.

Figure 5:
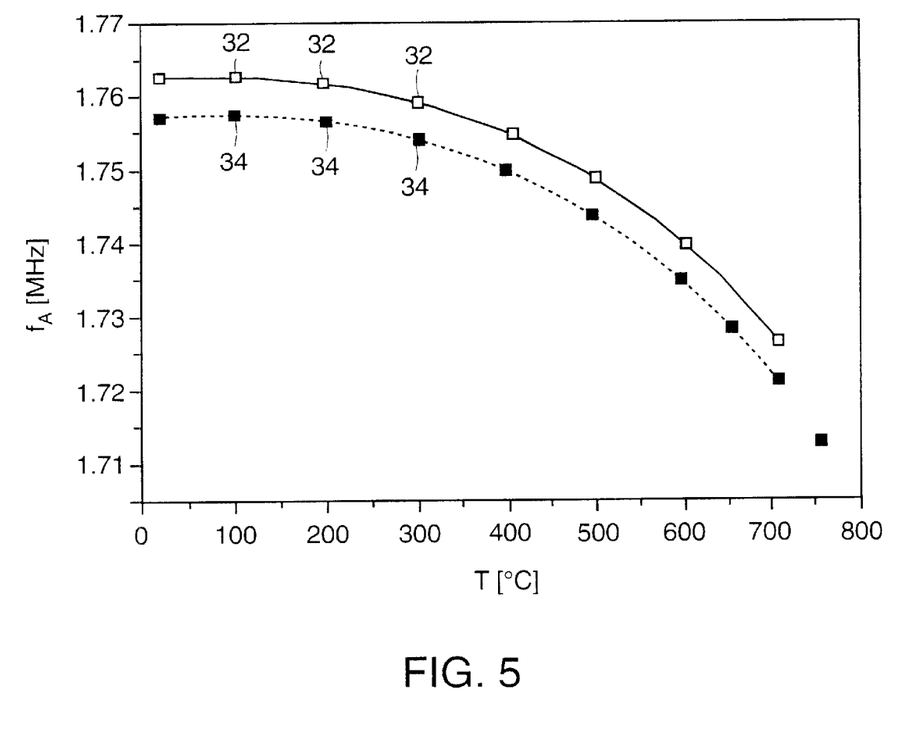
FIG. 5 is a plot of antiresonance frequency versus temperature for a balance with different masses deposited thereon.

Finally, a reference resonator 11, shielded from film deposition by a shutter 13, is mounted in the chamber to provide compensation for temperature sensitivity in the balance 10. Other than its being shielded from film deposition, the reference resonator 11 is identical or substantially identical to the balance 10. Accordingly, shifts in resonance or anti-resonance frequency of the balance 10 owing to shifts in temperature (which is evident in FIG. 5) can be effectively compensated by subtracting the change in frequency of the reference resonator 11 from the change in frequency of the balance 10 if the balance 10 and reference resonator 11 are maintained at the same temperature. Since te temperature sensitivities of the balance 10 and reference resonator 11 are identical or substantially identical, the difference between the frequency change of the reference resonator 11 and the frequency change of the balance 10 can be attributed to a change in the mass of film 17 deposited on the balance 10.

Figure 3:
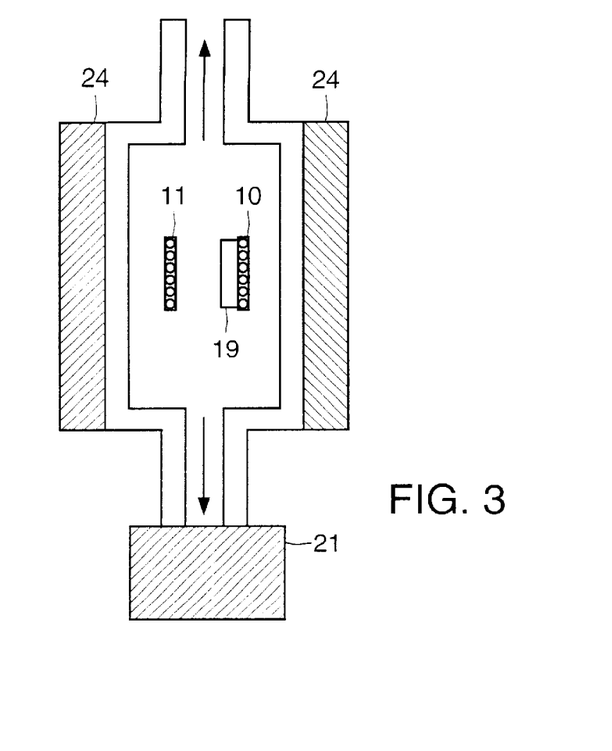
FIG. 3 is a thermogravimetric analysis (TGA) chamber including a high-temperature piezoelectric balance.

In another preferred embodiment, illustrated in FIG. 3, the balance 10 is coated with a film of a composition of interest to be subjected to thermogravimetric analysis by using a heater 24 to cycle the film 19 through a range of elevated temperatures and monitoring the change in mass as a function of temperature and/or atmosphere. Like the deposition chamber, the TGA chamber also includes a reference resonator 11, which is positioned to be at substantially the same temperature as the balance 10, for compensating for temperature sensitivity of the balance 10.

The TGA chamber can further include a gas source 21 for supplying a gaseous species subject to uptake by the film via a reaction process, such as oxidation or sulfidation. For example, oxygen can be supplied by the gas source 21 to oxidize an aluminum film to form aluminum oxide or to oxidize iron to form iron oxide. Alternatively, the gas source 21 can supply sulfur to react with a copper film, for example, to form copper sulfide. In other embodiments, where one wishes to know, for example, the oxygen content of a solid, the gas source 21 supplies a reducing gas, such as hydrogen, to extract the oxygen from the solid. Yet another embodiment is directed to applications where one wants to study the nonstoichiometry of a solid as a function of temperature and gas atmosphere. For example, high-temperature superconductors tend to lose oxygen upon heating and absorb oxygen upon cooling. The amount lost or gained depends on the oxygen content of the gag. In this embodiment, the gas source 21 supplies a mixture of argon and oxygen in a well-defined ratio.

The practice of heating the workpiece 16 and balance 10 to substantially-identical high temperatures is an important feature of this invention because a deposited film will, to some extent, re-evaporate from a workpiece on which it is deposited. The rate at which the deposited material re-evaporates generally increases with increasing temperature. By matching the temperature of the balance to that of the workpiece, a more accurate reading can be obtained than if the balance remains cool because the temperature-dependent rates of deposition and evaporation, for example, on the balance match those of the workpiece.

As a film is deposited or evaporated, the resonance or antiresonance frequency of the balance 10 is measured. These measurements can be taken at a fixed temperature or as the balance 10 and workpiece 16 are ramping up or ramping down in temperature. As material is deposited, the resonance and antiresonance frequencies of the balance 10 decrease. Conversely, as material evaporates from the balance 10, the resonance and antiresonance frequencies increase. Where the balance 10 comprises langasite, the antiresonance frequency (rather than the resonance frequency) preferably is used as the characteristic frequency because of the steeper slope at zero crossing of the imaginary part of the impedance in comparison to that of the resonance frequency. As will be discussed, below, the resultant change in mass can then be measured as a function of the change in anti-resonance or resonance frequency.

In contrast to the use of conventional piezoelectric balances in room-temperature applications, the balances of this invention have a bulk resistivity, $R_p$, at high temperature that can not be neglected because $R_p$ can become sufficiently small at elevated temperatures to attenuate the resonance signal. Consequently, an equivalent electrical circuit, illustrated in FIG. 4, includes an additional resistor $R_p$. Variable, $C_p$, is the bulk capacitance, which is largely temperature independent. Variable, $R_s$, is the dissipative resistance loss connected with resonance. Variable, $C_s$, is the dissipative capacitance loss connected with resonance; and variable, $L_s$, is the dissipative inductance loss connected with resonance.

Figure 4:
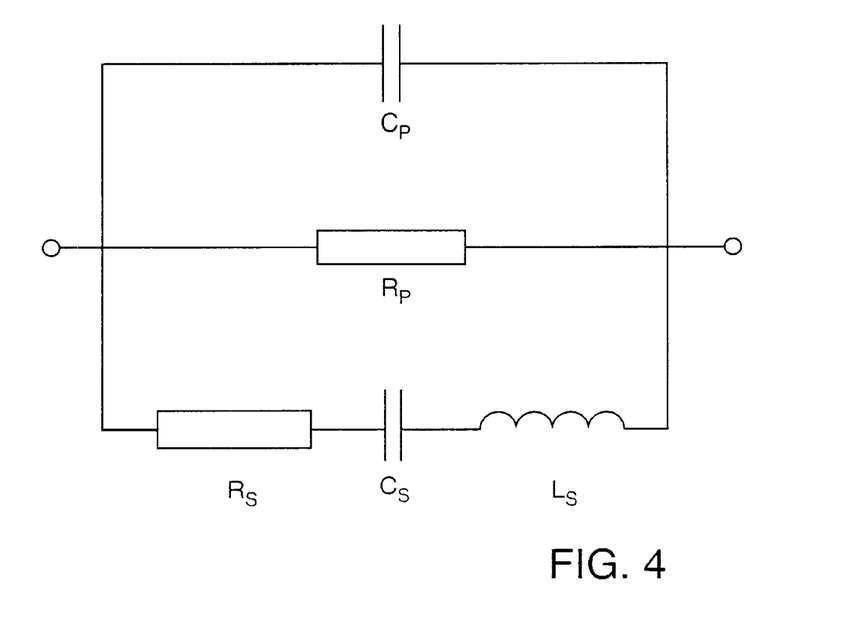
FIG. 4 is an electrical circuit equivalent to a high-temperature piezoelectric balance of this invention.

The resonance frequency of the balance can be approximated by the following function:

$$f_R \approx \frac{1}{2\pi\sqrt{L_S C_S}} \tag{1}$$

Further, the mass sensitivity of the balance, expressed in terms of change in resonance frequency as a function of change in mass, can be calculated as follows:

$$\Delta f_R = -\frac{2 f_R^2}{A\sqrt{\mu_0 \rho_0}} \Delta m \tag{2}$$

where the $f_R$ in the numerator is the initial resonance frequency; A is the exposed surface area of the balance; $\mu_0$ is the effective shear modulus of the balance; and $\rho_0$ is the density of the balance. Defining a mass-sensitivity coefficient, $k_R$, as follows:

$$k_R = -\frac{A\sqrt{\mu_0 \rho_0}}{2 f_R^2} \tag{3}$$

and solving for $\Delta m$ provides the following simplified equation for measuring a change in mass as a function of change in resonance frequency:

$$\Delta m = k_R \Delta f_R \tag{4}$$

Meanwhile the anti-resonance frequency of the balance can be approximated as follows:

$$f_A \approx \frac{1}{2\pi}\sqrt{\frac{C_P + C_S}{L_S C_P C_S}} \approx f_R \sqrt{1 + \frac{C_S}{C_P}} \tag{5}$$

The mass sensitivity of the balance, expressed in terms of change in anti-resonance frequency as a function of change in mass can be calculated as follows:

$$\Delta f_A \approx -\frac{2f_A^2}{A}\sqrt{\frac{C_P}{\mu_0\rho_0(C_p+C_s)}}\Delta m, \quad (6)$$

where the $f_A$ in the numerator is the initial anti-resonance frequency. Defining a mass-sensitivity coefficient, $k_A$, as follows:

$$k_A = -\frac{A}{2f_A^2}\sqrt{\frac{\mu_0\rho_0(C_P+C_S)}{C_P}} \quad (7)$$

and solving for $\Delta m$ provides the following simplified equation for measuring a change in mass as a function of change in anti-resonance frequency:

$$\Delta m = k_A \Delta f_A. \quad (8)$$

Comparing the mass loading sensitivity of a langasite balance with that of a quartz balance, one finds that the ratio of the mass loading sensitivity of the two materials, $K_Q/k_L$, is equal to 0.56 where the balances have identical resonance frequencies. In contrast to quartz, however, the mass loading sensitivity of langasite maintains to temperatures of up to 750° C. The lower sensitivity of langasite balances may be compensated easily by increasing the resonance frequency as a result of using thinner balances or the excitation of overtones, as is evident from the following equation:

$$f_R = \frac{n}{2l}\sqrt{\frac{\mu_0}{\rho_0}}, \quad (9)$$

where l and n are the balance thickness and the number of overtones (fundamental mode: n=1), respectively.

Balances of this invention can be used in a variety of applications including the following: in situ deposition rate monitoring during vapor-phase deposition processes, thermogravimetric analyses of small volumes, and monitoring post-growth annealing processes such as oxidation or reduction. When used for these and other high-temperature applications, the apparatus and methods of this invention can be used to measure high-temperature changes in mass (resulting, e.g., from deposition and evaporation) directly and with improved response time. As discussed, above, a balance used in situ for monitoring deposition rates is placed in the hot zone of a deposition chamber at the site of deposition. The balance thereby measures the growth of a deposited film formed by vapors that have reacted to form a solid product on the surface of the workpiece. Similarly, the balance is used to measure the small change in mass that occurs in an annealing process, such as when oxygen is added to the crystal structure of a film during post-growth oxidation. The balance likewise measures evaporation rates, i.e., the rate at which solids or chemical components of solids on the balance are converted to a vapor phase. Where the balance is used for thermogravimetry, typically using small volumes, the balance can provide precise measurements of evaporation and/or vapor-phase etching rates, oxygen loss or gain, oxidation and/or sulfidation rates, and isotope exchange kinetics (e.g., $^{16}O/^{18}O$).

EXEMPLIFICATION

The invention is further illustrated by the following example. It is to be understood, however, that although this example may specifically describe particular embodiments of this invention, it is primarily for purposes of illustration, and the invention in its broader aspects is not to be construed as limited thereto.

In this example, a pair of key-hole-shaped platinum electrodes were attached to a polished langasite plate having a thickness of 0.78 mm and a diameter of 19 mm. A pair of leads were respectively joined to the electrodes and to a model 4192A impedance analyzer (manufactured by Hewlett Packard) to form a circuit through the langasite plate. The langasite plate was heated, and the impedance of the device was monitored with the impedance analyzer in the vicinity of the resonance frequency to confirm the existence of bulk oscillations at high temperatures. The plate was then cycled from 20° C. to 750° C. and the antiresonance frequency of the plate was measured at selected intervals.

Additional platinum was then deposited onto the contacts and the langasite plate was again cycled through a temperature range with the antiresonance frequency measured at similar intervals. These latter measurements 34 are compared with the original measurements 32 in the graph illustrated in FIG. 5. As is evident from FIG. 5, lower antiresonance frequencies 34 were recorded when the additional mass was added to the contacts.

The table, below, provides the antiresonance frequency and other electrical properties of an equivalent circuit as measured in the original measurements.

| T [° C.] | $f_A$ [Hz] | $C_S$ [pF] | $R_S$ [Ω] | $\mu_o$ [$10^{10}$ N/m$^2$] | $k_A$ [μg/Hz] |
|---|---|---|---|---|---|
| 20 | 1763082 | 0.48 | 27 | 4.29 | −0.0972 |
| 103 | 1762924 | 0.31 | 33 | 4.31 | −0.0969 |
| 198 | 1761503 | 0.42 | 21 | 4.29 | −0.0971 |
| 300 | 1758400 | 0.59 | 15 | 4.25 | −0.0976 |
| 402 | 1754044 | .067 | 31 | 4.22 | −0.0979 |
| 502 | 1748499 | 0.80 | 145 | 4.16 | −0.0985 |
| 602 | 1739485 | 1.03 | 435 | 4.10 | −0.0994 |
| 701 | 1725984 | 1.35 | 770 | 3.99 | −0.1007 |

The bulk capacity ($C_P$) of the balance was determined to be 28.4 pF from measurements made by the impedance analyzer. The bulk resistance ($R_P$) of the balance over the temperature range of 500° C. to 900° C. was found to fit the following equation:

$$R_P = 10^{-1} e^{12629/T} K\Omega, \quad (10)$$

where T is measured in Kelvin.

In this example, the antiresonance frequency (rather than the resonance frequency) was monitored due to the steeper slope at zero crossing of the imaginary part of the impedance, as noted above.

Knowing the values exhibited in the above table across the indicated temperature range, changes in the resonance frequency can be correlated to change in mass using Equation 5, wherein $\Delta m = k_A \Delta f_A$.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of monitoring a change in mass of a thin film on a workpiece comprising:
   heating the workpiece to a temperature above about 500° C.;
   providing a piezoelectric balance including a piezoelectric material selected from a group of piezoelectric materials consisting of $Ca_3Ga_2Ge_4O_{14}$ structure materials and members of the (Al, Ga)N system at approximately the temperature of the heated workpiece;
   changing the mass of the thin film on both the piezoelectric balance and the heated workpiece within a deposition chamber including a vapor, the thin film being exposed to the vapor; and
   monitoring the frequency response of the piezoelectric balance to monitor the mass of film on the heated workpiece.

2. The method of claim 1, wherein the workpiece and piezoelectric balance are heated to a temperature of about 600° C. or higher while monitoring the frequency response of the piezoelectric balance.

3. The method of claim 1, wherein the piezoelectric balance includes a piezoelectric material that is stable and retains its piezoelectric properties at temperatures above about 500° C.

4. The method of claim 1, wherein the piezoelectric balance includes langasite.

5. The method of claim 1, wherein the thin film is deposited simultaneously both on the piezoelectric balance and on the heated workpiece.

6. The method of claim 1, wherein the mass of the thin film is changed by deposition.

7. The method of claim 6, wherein the mass of the thin film is changed by chemical vapor deposition.

8. The method of claim 6, wherein the mass of the thin film is changed by physical vapor deposition.

9. The method of claim 1, wherein the mass of the thin film is changed by vaporization.

10. The method of claim 1, wherein the mass of the thin film is changed by oxidation or reduction.

11. A method of monitoring a change in mass of a thin film on a workpiece comprising:
    heating the workpiece;
    providing a piezoelectric balance at approximately the temperature of the heated workpiece;
    changing the mass of the thin film on both the piezoelectric balance and the heated workpiece;
    changing the temperature of the workpiece and the piezoelectric balance; and
    monitoring the frequency response of the piezoelectric balance to monitor the mass of film on the heated workpiece.

12. A method of measuring change in mass of a film as a function of temperature comprising:
    heating the workpiece;
    providing a piezoelectric balance at approximately the temperature of the heated workpiece;
    changing the mass of the film on both the piezoelectric balance and the heated workpiece; and
    monitoring the frequency response of the piezoelectric balance as a function of temperature.

13. The method of claim 12, wherein the workpiece and piezoelectric balance are heated to a temperature above about 500° C. while monitoring the frequency response of the piezoelectric balance.

14. The method of claim 13, wherein the workpiece and piezoelectric balance are heated to a temperature of about 600° C. or higher while monitoring the frequency response of the piezoelectric balance.

15. The method of claim 12, wherein the piezoelectric balance includes a piezoelectric material that is stable and retains its piezoelectric properties at temperatures above about 500° C.

16. The method of claim 12, wherein the piezoelectric balance includes a piezoelectric material having a $Ca_3Ga_2Ge_4O_{14}$ structure.

17. The method of claim 12, wherein the piezoelectric balance includes a member of the (Al,Ga)N system.

18. The method of claim 12, wherein the piezoelectric balance includes gallium phosphate.

19. The method of claim 12, wherein the piezoelectric balance includes langasite.

20. The method of claim 13, wherein the thin film is deposited simultaneously both on the piezoelectric balance and on the heated workpiece.

21. The method of claim 13, wherein the mass of the thin film is changed by deposition.

22. The method of claim 21, wherein the mass of the thin film is changed by chemical vapor deposition.

23. The method of claim 21, wherein the mass of the thin film is changed by physical vapor deposition.

24. The method of claim 13, wherein the mass of the thin film is changed by vaporization.

25. The method of claim 13, wherein the mass of the thin film is changed by oxidation or reduction.

26. A method of measuring change in mass of a film as a function of gas composition comprising:
    heating the workpiece;
    providing a piezoelectric balance at approximately the temperature of the heated workpiece;
    changing the mass of the film on both the piezoelectric balance and the heated workpiece; and
    monitoring the frequency response of the piezoelectric balance as a function of gas composition to which the film is exposed.

27. A method of monitoring change in mass of a thin film on a heated workpiece comprising:
    providing a piezoelectric balance including a piezoelectric material selected from a group of piezoelectric materials consisting of $Ca_3Ga_2Ge_4O_{14}$ structure materials and members of the (Al, Ga)N system;
    changing the mass of the thin film on both the piezoelectric balance and the heated workpiece within a deposition chamber including a vapor, the thin film being exposed to the vapor; and
    monitoring the frequency response of the piezoelectric balance to monitor the mass of film on the heated workpiece.

28. The method of claim 27, wherein the piezoelectric balance includes langasite.

29. A method for thermogravimetric analysis of a solid film of a composition comprising:
    providing a piezoelectric balance;
    depositing the solid film of the composition on the piezoelectric balance;
    while exposing the solid film to a gas, scanning the temperature of the piezoelectric balance through a range of temperatures; and
    monitoring the frequency response of the piezoelectric balance to monitor the change in mass of the composition as a function of temperature.

30. The method of claim 29, wherein the piezoelectric balance is heated to a temperature above about 500° C. while monitoring the frequency response of the piezoelectric balance.

31. The method of claim 29, wherein the piezoelectric balance includes langasite.

32. A method for thermogravimetric analysis of a film as a function of gas composition comprising:

providing a piezoelectric balance;

depositing the film on the piezoelectric balance;

changing the composition of gas to which the film is exposed; and monitoring the frequency response of the piezoelectric balance to monitor the change in the mass of the film as a function of the gas composition.

33. The method of claim 32, wherein the piezoelectric balance is heated to a temperature above about 500° C. while monitoring the frequency response of the piezoelectric balance.

34. The method of claim 32, wherein the piezoelectric balance includes langasite.

35. An apparatus for depositing a film on a workpiece, comprising:

a vessel defining a deposition chamber;

a source of vapor having access to the deposition chamber, wherein the vapor can be deposited on a workpiece within the deposition chamber;

a heater within the deposition chamber; and a piezoelectric balance within the deposition chamber and thermal communication with the heater and positioned to be coated with a film comprising deposited vapor, wherein the piezoelectric balance includes a piezoelectric material selected from the group consisting of $Ca_3Ga_2Ge_4O_{14}$ structure materials, members of the (Al, Ga)N system, and gallium phosphate.

36. The apparatus of claim 35, wherein the piezoelectric balance includes langasite.

37. The apparatus of claim 35, further comprising an impedance analyzer electrically coupled to the piezoelectric balance.

38. An apparatus for performing thermogravimetric analysis, comprising:

a vessel defining a thermogravimetric analysis chamber;

a heater within the chamber; and a piezoelectric balance within the chamber and in thermal communication with the heater and coated with a composition subject to thermogravimetric analysis, the piezoelectric balance including a piezoelectric material that is stable at high temperatures, the piezoelectric material selected from the group consisting of $Ca_3Ga_2Ge_4O_{14}$ structure materials, members of the (Al, Ga)N system, and gallium phosphate.

39. The apparatus of claim 38, wherein the piezoelectric balance includes langasite.

40. The apparatus of claim 38, further comprising an impedance analyzer electrically coupled to the piezoelectric balance.

* * * * *